United States Patent [19]

Eakins et al.

[11] 4,188,394

[45] Feb. 12, 1980

[54] OPHTHALMIC COMPOSITION AND METHOD OF USE

[75] Inventors: Kenneth E. Eakins, Sparkill; Parimal Bhattacherjee, Nyack, both of N.Y.

[73] Assignee: Nelson Research & Development Company, Irvine, Calif.

[21] Appl. No.: 903,586

[22] Filed: May 8, 1978

[51] Int. Cl.² .............................................. A61K 31/475
[52] U.S. Cl. ..................................................... 424/262
[58] Field of Search ......................................... 424/262

[56] References Cited
U.S. PATENT DOCUMENTS 3,097,137  7/1963  Beer et al. ............................ 424/195
3,749,784  7/1973  Johnson ................................ 424/262

OTHER PUBLICATIONS

Acta. Physiol. Scand., 1976, 98, 425–432.
Physician's Desk Reference, 30th ed., 1976, Published by Medical Economics Co., N.J., pp. 987 and 988.

Primary Examiner—Donald B. Moyer
Attorney, Agent, or Firm—Martin A. Voet

[57] ABSTRACT

A therapeutic composition comprising a topically administrable ophthalmic pharmaceutical carrier and vinblastine. The fore-going composition temporarily alleviates the symptoms of glaucoma when topically administered to the eye.

8 Claims, No Drawings

OPHTHALMIC COMPOSITION AND METHOD OF USE

BACKGROUND OF THE INVENTION

1. Field of the Invention

The invention relates generally to a composition and method for reducing intraocular pressure (IOP) in humans and animals. More particular, the invention relates to a method for temporarily alleviating the symptoms of glaucoma.

2. Background of the Prior Art

Vinblastine is an alkaloid isolated from *Vinca rosea* Linn., Apocynaceae whose extraction procedure is well-known in the art, see for example, U.S. Pat. Nos. 3,097,137 and 3,225,030. Vinblastine has been used heretofore in research and as an antineoplastic agent.

Glaucoma is a condition of the eye characterized by increased intraocular pressure. Untreated, the condition eventually leads to irreversible retinal damage and blindness. Conventional therapy for glaucoma is with pilocarpine and/or epinephrine administered topically several times daily.

One of the problems with many conventional drugs for the treatment of glaucoma is that they decrease the size of the pupil, i.e., they are miotic drugs. This is an undesirable side effect, resulting in temporarily impaired vision.

SUMMARY OF THE INVENTION

There has now been discovered a method of reducing IOP and for treating glaucoma in which there is a minimum of miotic side effects.

The present invention relates to a therapeutic composition comprising a topically administrable ophthalmic pharmaceutical carrier and an effective amount of vinblastine.

The present invention also relates to a method for temporarily alleviating the symptoms of glaucoma in humans comprising topically administering to the eyes of human having glaucoma an effective amount of the foregoing composition.

DESCRIPTION OF THE INVENTION

Suitable ophthalmic carriers are known to those skilled in the art and all such conventional carriers may be employed in the present invention. Thus, a particular carrier may take the form of a sterile, ophthalmic ointment, cream, gel, solution, or dispersion. Also included in suitable ophthalmic carriers are slow release polymers, e.g., "Ocusert" polymers, "Hydron" polymers, etc. Stabilizers may also be used such as, for example, chelating agents, e.g., EDTA. Antioxidants may also be used, e.g., sodium bisulfite, sodium thiosulfite, 8-hydroxy quinoline or ascorbic acid. Sterility typically will be maintained by conventional ophthalmic preservatives, e.g., chlorbutanol, benzalkonium chloride, cetylpyridium chloride, phenyl mercuric salts, thimerosal, etc., for aqueous formulations, and used in amounts with are nontoxic and which generally vary from about 0.001 to about 0.1% by weight of the aqueous solution. Conventional preservatives for ointments include methyl and propyl parabens. Typical ointment bases include white petrolatum and mineral oil or liquid petrolatum. However, preserved aqueous carriers are preferred. Solutions may be manually delivered to the eye in suitable dosage form, e.g., eye drops, or delivered by suitable microdrop or spray apparatus typically affording a metered dose of medicament. Examples of suitable ophthalmic carriers include sterile, substantially isotonic, aqueous solutions containing minor amounts, i.e., less than about 5% by weight hydroxypropylmethylcellulose, polyvinyl alcohol, carboxymethylcellulose, hydroxyethylcellulose, glycerine and EDTA. The solutions are preferably maintained at substantially neutral pH and isotonic with appropriate amounts of conventional buffers, e.g., phosphate, borate, acetate, tris, etc.

A preferred ophthalmic composition is a preserved aqueous solution containing the following ingredients at the indicated concentration.

Vinblastine—Wt. percent-1
Stabilizer—Wt. percent-0.01
Preservative—Wt. percent-0.005
Buffer—M-0.05
NaCl q.s. ad isotonic.
Water q.s. ad 100 percent.

The amount of vinblastine to be used in the therapeutic treatment of glaucoma will vary with the age of the patient and the severity of the glaucoma. Generally a dose level of one or two drops of the foregoing aqueous solution 1-4 times daily would be a suitable dosage amount. Generally, the concentration of vinblastine will vary between about 0.01 and about 5 and preferably between about 0.1 and 2%.

EXAMPLE I

A study on the effect of topical administration of vinblastine on New Zealand white rabbit intraocular pressure was performed. Drug solutions in phosphate buffer, pH 7.5, were instilled onto the cornea in a constant volume of 20 μl, control eyes receiving vehicle only. IOP was measured with a pneumatic tonometer and is shown as the difference between the treated and control eyes. Four or five animals were used for each concentration. Table 1 below shows the results of the study.

Table 1

| Concentration of Vinblastine | Change in IOP (mmHg) | | |
|---|---|---|---|
| | 0 hrs | 24 hrs | 48 hrs |
| .02 | 0 | −1.4 | −2.1 |
| 0.1 | 0 | −7.5 | −9.5 |

We claim:

1. A method for reducing intraocular pressure in humans and animals comprising topically administering to the eye of a human or animal having elevated intraocular pressure an effective, intraocular pressure reducing amount of vinblastine together with a suitable ophthalmic pharmaceutical carrier.

2. The method of claim 1 wherein the carrier is a preserved, aqueous solution.

3. The method of claim 1 wherein an effective amount of vinblastine is between about 0.01% and about 5%.

4. The method of claim 1 wherein an effective amount of vinblastine is between about 0.1% and 2%.

5. A method for treating glaucoma in humans comprising topically administering to the eye of a human having glaucoma an effective, intraocular pressure reducing amount of vinblastine together with a suitable ophthalmic carrier.

6. The method of claim 5 wherein the carrier is a preserved aqueous solution.

7. The method of claim 5 wherein an effective amount of vinblastine is between about 0.01% and 5%.

8. The method of claim 5 wherein an effective amount of vinblastine is between about 0.1% and 2%.